United States Patent
Cook

(10) Patent No.: US 6,468,233 B2
(45) Date of Patent: Oct. 22, 2002

(54) POSTURE ANALYZER

(76) Inventor: Gerry Cook, P.O. Box 1006, Sandpoint, ID (US) 83864

( * ) Notice: Subject to any disclaimer, the term of this patent is extended or adjusted under 35 U.S.C. 154(b) by 0 days.

(21) Appl. No.: 09/892,907

(22) Filed: Jun. 26, 2001

(65) Prior Publication Data

US 2002/0049393 A1 Apr. 25, 2002

Related U.S. Application Data

(60) Provisional application No. 60/214,179, filed on Jun. 26, 2000.

(51) Int. Cl.[7] ............................................. A61B 5/103
(52) U.S. Cl. ..................................... 600/594; 33/514.2
(58) Field of Search ................................ 600/594, 587; 33/514.2

(56) References Cited

U.S. PATENT DOCUMENTS

| | | | |
|---|---|---|---|
| 341,572 A | * 5/1886 | Hand | ........................ 33/514.2 |
| 668,228 A | 2/1901 | Smith | |
| 874,091 A | * 12/1907 | Lemcke | ..................... 33/514.2 |
| 889,224 A | 6/1908 | Haas | |
| 1,205,826 A | 11/1916 | Wentworth | |
| 1,234,527 A | 7/1917 | Berriman | |
| 1,271,461 A | 7/1918 | Hanna | |
| 1,846,528 A | 2/1932 | Santin | |
| 2,111,648 A | 3/1938 | Stone | |
| 2,136,134 A | 11/1938 | Holley | |
| 2,196,114 A | 4/1940 | Holley | |
| 2,295,447 A | 9/1942 | Bierman | |
| 2,324,672 A | * 7/1943 | Bierman et al. | ............. 600/594 |
| 4,425,713 A | * 1/1984 | Rotella | ........................ 600/587 |
| 4,723,557 A | * 2/1988 | Gross | ........................ 600/594 |
| 5,101,835 A | 4/1992 | DelRe | |
| 5,471,995 A | 12/1995 | Halliday | |

* cited by examiner

*Primary Examiner*—Stephen M. Hepperle
(74) *Attorney, Agent, or Firm*—Richard C. Conover

(57) ABSTRACT

A posture analyzer for analyzing a patient's spine having an upright standard secured to a base resting on a floor. A rectangular frame has one side frame member secured to the upright standard at a selected height. The frame member supports a markable panel, which panel includes an orthogonal grid pattern and a normal spine depiction on the panel. A bar holder is slidably secured to a second side frame member. The bar holder is moveable in the vertical direction along the second side frame member. The bar holder includes means for slidably holding a bar which extends in a horizontal direction parallel to the planar surface of the panel. A roller is secured to an end of the bar for rolling up and down a patient's spine, and a pen is secured to the opposite end of the bar for marking on the planar surface of the panel. When the roller is moved vertically and horizontally along a patient's spine, the pen makes a corresponding tracking mark on the panel.

5 Claims, 2 Drawing Sheets

POSTURE ANALYZER

This application claims the benefit of provisional application 60/214,179 filed on Jun. 26, 2000.

BACKGROUND OF INVENTION

The present invention relates to a posture analyzer for graphically determining the variance between the curvature of a patient's spine with the curvature of a "normal" spine.

When the curvature of the spine differs from a normal curve, problems may occur such as lower back pain or forward lean. Further, if the spine is curved laterally, a condition known as scoliosis occurs.

A need exists for an inexpensive, easy-to-use apparatus for accurately showing a patient's spinal curve, both graphically and quantitatively.

A graphic display of a patient's spine is needed to show visually the difference between the patient's spine and a normal spine. Quantitative information is needed for computer processing where software is used to analyze the curvature of a spine of a patient. Once the shape of the spine is known, corrective action can be planned to change the curvature of the spine to conform with a more normal curvature. With the present invention, specific vertebrae can be identified which need to be moved.

Finally, a need exists for apparatus which can be used to inexpensively monitor any corrective action done to change the curvature of the spine.

SUMMARY OF INVENTION

A posture analyzer for analyzing a patient's spine having an upright standard secured to a base resting on a floor. A rectangular frame has one side frame member secured to the upright standard at a selected height. The frame member supports a markable panel, which panel includes an orthogonal grid pattern and a normal spine depiction on the panel. A bar holder is slidably secured to a second side frame member. The bar holder is moveable in the vertical direction along the second side frame member. The bar holder includes means for slidably holding a bar which extends in a horizontal direction parallel to the planar surface of the panel. A roller is secured to an end of the bar for rolling up and down a patient's spine, and a pen is secured to the opposite end of the bar for marking on the planar surface of the panel. When the roller is moved vertically and horizontally along a patient's spine, the pen makes a corresponding tracking mark on the panel.

DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 1:
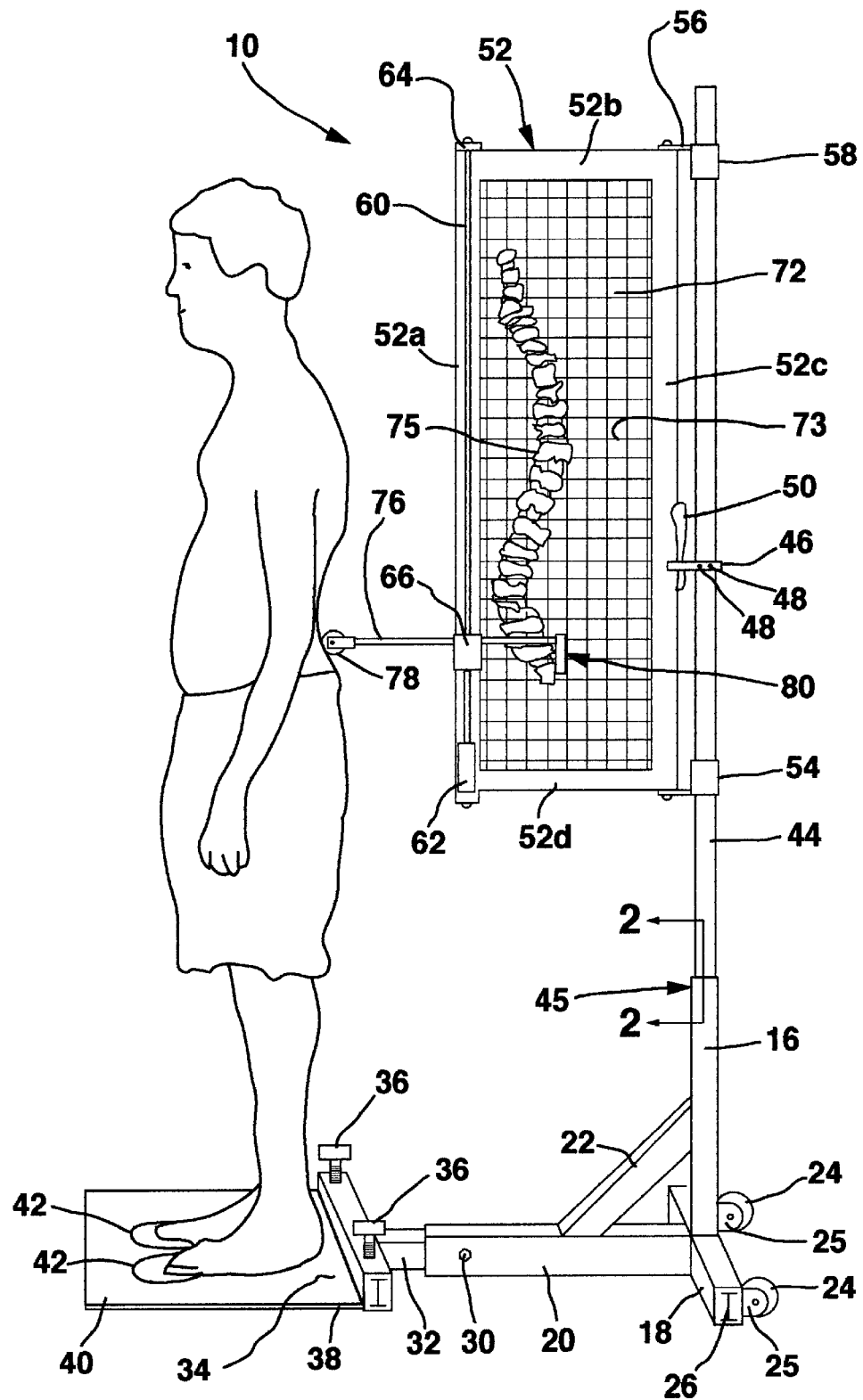
FIG. 1 is a perspective front elevational view of a posture analyzer of the present invention.

A posture analyzer 10 is shown in FIG. 1. A tubular upright 16 has a lower end fixedly connected to a mid-section of an elongate base member 18. Base member 18 is positioned in an orthogonal relation with upright 16. A base tube 20 is fixedly connected to base member 18 in orthogonal relation with base member 18 and upright 16. A brace 22 is positioned to extend between upright 16 and base tube 20, and is fixedly attached thereto. In a preferred embodiment, base member 18 is a tube and is provided with end caps 26 inserted in each end to prevent dirt from entering the tube.

As shown in FIG. 1, a pair of spaced apart wheels 24, rotatably held in yokes 25, extend away from base member 18 on a side opposite the connection to base tube 20. Yokes 25, holding wheels 24, are fixedly attached to base 18 so that wheels 24 are positioned to be slightly above a floor whenever base tube 20 rests on the floor as shown in FIG. 1.

The base tube 20 includes a threaded holding bolt 30 threaded into a hole (not shown) extending from the exterior to the interior of base tube 20.

A telescoping member 32 is slidably received by base tube 20. Holding bolt 30 secures member 32 within tube 20 at a selected position. Telescoping tube 32 has its free end fixedly connected perpendicularly to the mid section of tilt-adjusting tube 34. Tilt-adjusting tube 34 extends substantially parallel with base member 18. Tilt-adjusting tube 34 includes a pair of threaded bolts 36. Each bolt 36 includes a finger hold at one end and is threaded through corresponding holes (not shown) in tilt-adjusting tube 34. The bolts 36 extend upwardly in a direction substantially parallel with upright 16, as shown, and extend downwardly through tube 34 to abut the floor. Bolts 36 can be used to tilt the upright 16 to a vertically upright position. Tilt-adjusting tube 34 also has end caps 38 inserted into each end to again keep dirt out of the interior of the tube.

A rectangular foot mat 40 is placed with one edge positioned against tilt-adjusting tube 34 as shown. Foot mat 40 has foot placement markers 42 printed on the mat to indicate where a patient is to stand on the mat.

Figure 2:
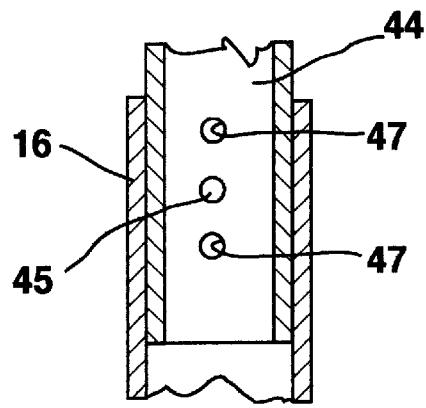
FIG. 2 is a detail cross-section taken along the lines 2—2 in FIG. 1.

As shown in FIG. 1, tubular standard 44 is telescopically inserted in tubular upright 16. As shown in FIG. 2, standard 44 is provided with a plurality of adjustment holes 47. A pin 45, as shown in FIG. 1, is inserted through a corresponding hole (not shown) in upright 16 and then through one of the selected holes 47 in standard 44. This structure adjustably holds standard 44 at a selected vertical height with respect to upright 16.

A pen container 46 is conventionally mounted to standard 44 and is held in place by set screws 48. Spare pens 50 can be temporarily held in pen container 46 by inserting them in holes that extend through the pen holder in a direction that, is substantially parallel with standard 44.

A rectangular frame 52 is provided having sides 52a, 52b, 52c, and 52d. A lower bracket 54 and an upper bracket 56 each have one end slidably connected to standard 44. The other ends of brackets 54 and 56 are secured to frame side 52c. A threaded bolt 58 is provided which extends through a threaded hole (not shown) in bracket 56 and abuts standard 44. By tightening bolt 58, the frame 52 is secured to standard 44 at a selected vertical position. With this structural arrangement, rectangular frame 52 is positioned to extend substantially parallel with standard 44 and also in a plane that includes base tube 20.

Rectangular frame 52 supports plexiglass panel 72 within the interior of the frame using any of the conventional techniques known to those skilled in the art to hold a panel within a frame. As shown in FIG. 1, an orthogonal grid 73 and a "normal" side view of a spine 75 is screen printed on plexiglass panel 72.

A rod 60, which is spaced apart from but runs parallel to frame side 52a, is supported at both ends by rod holders 62 and 64 mounted to frame side 52a.

A block 66 has a first hole (not shown) drilled through the block, which hole is sized to slidingly receive rod 60. With this arrangement, block 66 can slide along the rod 60 with a minimum of "wobble."

A second hole (not shown) is drilled through the block which second hole is substantially perpendicular to the first hole. A slender bar 76 is slidingly received by the second hole in block 66 again so that bar 76 can slide in the second hole with a minimum of "wobble." Bar 76 is provided with a conventional roller assembly 78 mounted to the bar 76 which extends in a direction away from standard 44. When the roller assembly 78 is moved upwardly or downwardly, the bar 76 is constrained to travel in a plane parallel to the plane of plexiglass panel 72.

Figure 3:
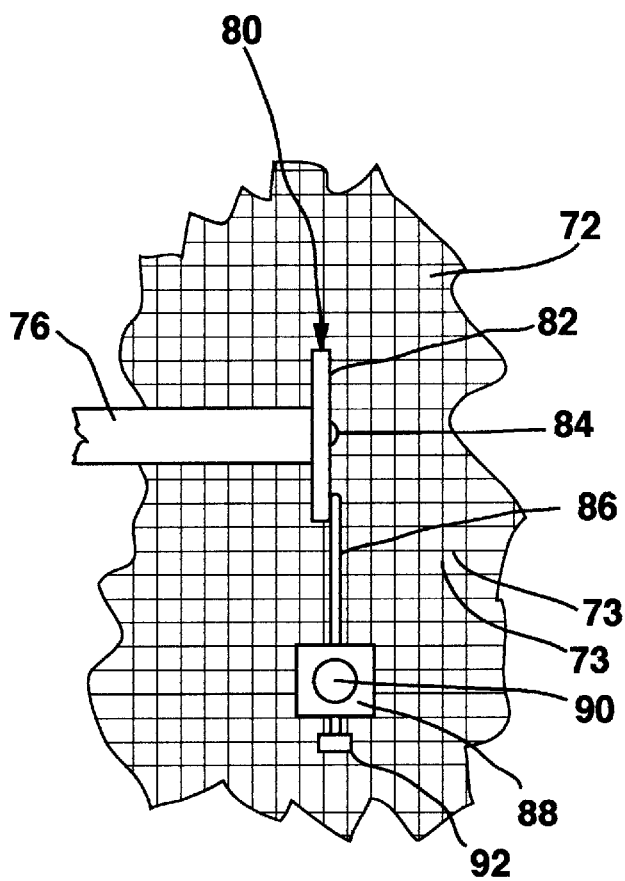
FIG. 3 is an elevational view of a pen holder assembly shown in FIG. 1.
Figure 4:
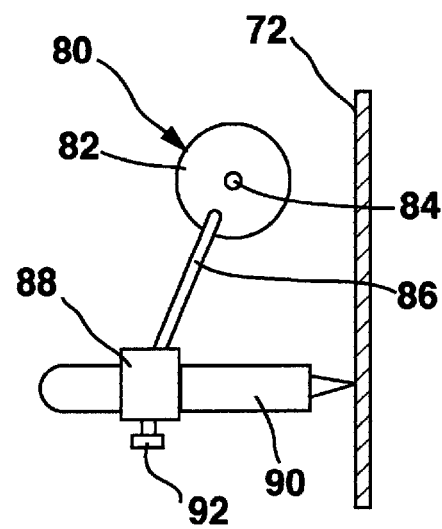
FIG. 4 is a right side view of the pen holder assembly shown in FIG. 3.

At the opposite end of bar 76, a pen holder assembly 80 is pivotally mounted to the bar. As shown in FIGS. 3 and 4, pen holder assembly 80 includes a washer 82 that is held onto an end of rod 80 by a bolt 84. An arm 86 has one end fixedly connected to washer 82. A weight 88 is fixedly connected to the other end of arm 86. Weight 88 is provided with a hole (not shown) for slidingly receiving a pen 90 which is oriented with its marking end in abutment with the plexiglass panel 72. In a preferred embodiment, pen 90 uses erasable ink.

A threaded thumbscrew 92 extends from the exterior of weight 88 into the hole. Thumbscrew 92 can then be tightened against pen 90 to hold the pen within weight 88. As arm 86 is rotated away from the vertical as shown in FIG. 4, weight 88, being pulled down by gravity, forces pen 90 against plexiglass panel 72.

In operation, when the posture analyzer 10 is to be moved to another location, the standard 44 is first rotated to a position where wheels 24 contact the floor. Posture analyzer 10 can then be rolled to the new location where measurements are to be made. At the new location, standard 44 is allowed to rotate to an upright position where wheels 24 are again separated from the floor and analyzer 10 is support ed by base member 18, base tube 20 and tilt adjustment bolts 36. Bolts 36 can then be threadably rotated to position standard 44 to an essentially vertical position.

To prepare analyzer 10 for recording the curvature of a patient's spine, pin 45 is removed from standard 44 and upright 16. The standard 44 is extended to the appropriate vertical height and pin 45 inserted into the appropriate holes in standard 44 and upright 16 to secure the standard 44 at the selected vertical height.

A person stands on mat 40 with his feet aligned with foot markers 42 and his heels abutting tilt adjusting tube 34. Holding bolt 30 can then be loosened, and telescoping tube 32 moved to a position where weight 88 is properly positioned horizontally on plexiglass panel 72. The proper horizontal position is with the weight 88 located horizontally at the bottom of the "normal" spine printed on plexiglass panel 72. Holding bolt 30 can then be retightened.

Next threaded bolt 58 can be loosened and rectangular frame 52 adjusted in height vertically so that weight 88 is located vertically at the bottom of the "normal" spine printed on plexiglass panel 72. Threaded bolt 58 can then be retightened to secure this arrangement.

A pen 90 is then inserted into weight 88 and held in place by thumbscrew 92. Pen 90, being pivoted by weight 88, is pressed against plexiglass 72. The pen 90 should be positioned both vertically and horizontally at the bottom of the "normal" spine on panel 72.

An operator then presses roller assembly 78 against a patient's spine with one hand and slides the roller up the patient's spine while maintaining the roller against the spine. This movement causes pen 90 to draw on plexiglass panel 72 a line corresponding to the two-dimensional shape of the patient's spine along the "x" and "y" axis. The "x" axis being the axis from front to back of the patient, and the "y" axis being the vertical up and down axis of the patient.

The analyzer 10 is used to record, on the grid 73, a curve corresponding to the shape of a patient's spine. This curve is readily compared with a "normal" spine's curvature 75 located on panel 72. Grid coordinates, as found on grid 73 printed on panel 72, are read and can be entered into a computer. The computer can then analyze the variances and print out a report to describe the variance and possibly even the corrective actions required.

This posture analyzer 10 can also be used for measuring scoliosis of a patient. In this application, the pen 90 is removed from weight 88 and inserted in a conventional holder which replaces roller 78. Here the pen is moved vertically along the patient's spine making a vertical line up the patient's back. Measurements may be made of the spine curvature variations along the "z" and "y" axis of the spine where the "z" axis is the axis from side to side of the patient.

With this information, a three-dimensional analysis of a patient's spine can be made. Corrective action can then be done and the patient's progress can be monitored by using analyzer 10 to determine whether the curvature of the spine is becoming more normal.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims:

I claim:

1. A posture analyzer for analyzing a patient's spine comprising:

a base;

a vertically adjustable upright standard secured to the base;

a rectangular frame having a pair of spaced apart and parallel side frame members together with spaced apart and parallel top and bottom members;

means for securing a first side frame member to the upright standard at a selected height;

a markable panel having a planar surface supported by the frame;

means for slidably securing a bar holder to a second side frame member for movement in the vertical direction;

the bar holder.including means for slidably holding a bar which extends in the horizontal direction parallel to the planar surface of the panel;

a roller means secured to an end of the bar for rolling up and down a patient's spine;

a pen holder secured to an opposite end of the bar; and pen means received by the pen holder for marking on the planar surface of the panel;

whereby when the roller is moved vertically and horizontally along a patient's spine, the pen makes a corresponding tracking mark on the panel.

2. The posture analyzer according to claim 1 wherein the panel comprises a plexiglass panel having orthogonal grid markings and a depiction of a normal spine.

3. The posture analyzer according to claim 1 wherein the base includes adjustment means for locating the pen at a preselected horizontal position on the planar surface of the panel when the roller is positioned to abut a patient's spine.

4. The posture analyzer according to claim 1 wherein the means for slidably securing a bar holder to the second frame member includes a rod having its ends secured to the second frame member and the bar holder includes a hole for receiving the rod.

5. The posture analyzer according to claim 1 wherein the pen holder includes weight means for resiliently forcing the pen means against the planar surface of the panel.

* * * * *